United States Patent [19]
Treiber et al.

[11] Patent Number: 5,225,403
[45] Date of Patent: Jul. 6, 1993

[54] C-21 HYDROXYLATED FK-506 ANTAGONIST

[75] Inventors: Laszlo R. Treiber, Gillette; Georgette Dezeny, Short Hills; Lawrence F. Colwell, Jr., Eatontown; Byron H. Arison, Watchung; Francis Dumont, Rahway, all of N.J.

[73] Assignee: Merck & Co., Inc., Rahway, N.J.

[21] Appl. No.: 720,550

[22] Filed: Jun. 25, 1991

[51] Int. Cl.$^5$ .................. A01N 55/00; A61K 31/695
[52] U.S. Cl. ...................... 514/63; 514/291; 514/411; 540/452; 540/456; 435/118; 435/886; 435/898
[58] Field of Search .............. 514/291, 63, 411; 540/452, 456; 435/898, 886, 118

[56] References Cited

U.S. PATENT DOCUMENTS

| | | | |
|---|---|---|---|
| 3,244,592 | 4/1966 | Arai et al. | 424/115 |
| 4,894,366 | 1/1990 | Okuhara et al. | 514/291 |
| 5,064,835 | 11/1991 | Bochis et al. | 514/291 |

FOREIGN PATENT DOCUMENTS 0323042  7/1989  European Pat. Off. .

*Primary Examiner*—Nathan M. Nutter
*Attorney, Agent, or Firm*—Robert J. North; Joseph F. DiPrima; Charles M. Caruso

[57] ABSTRACT

Described is a process for producing a new FK-506 antagonist agent, a C-21 hydroxylated analog of FR-900520 under novel fermentation conditions utilizing the novel microorganism, *Streptomyces hygroscopicus* (Merck Culture Collection MA 6832) ATCC No. 55166. The macrolide antagonist is useful in preventing and/or counteracting accidental or inadvertent FK-506 overdosage in an FK-506 therapeutic program designed to prevent autoimmune diseases or human host rejection of foreign organ transplants, e.g. bone marrow, liver, lung, kidney and heart transplants.

6 Claims, 1 Drawing Sheet

C-21 HYDROXYLATED FK-506 ANTAGONIST

BACKGROUND OF THE INVENTION

1. Field of the Invention

This invention related to a new FK-506 antagonist agent, a C-21-hydroxy-FR-900520, a novel fermentation process for its production, utilizing the novel microorganism *Streptomyces hygroscopicus* (MA 6832), ATCC No. 55166. The process involves culturing the microorganism in the presence of FR-900520 under conditions which hydroxylate the $C_{21}$ carbon of FR-900520. Also disclosed is a method of its use for preventing and/or counteracting accidental or inadvertent FK-506 overdosage in a therapeutic program designed to prevent in a human host, autoimmune diseases, and/or organ transplant rejections.

2. Brief Description of disclosures in the Art

In 1983, the U.S. FDA licensed cyclosporin, and extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide immunosuppressant FK-506 which is reputed to be 100 times more effective than cyclosporin. The macrolide is produced by fermentation of a particular strain of *Streptomyces tsukubaensis*. Also described is the closely related macrolide immunosuppressant FR-900520, produced by *S. hygroscopicus* subsp. *yakushimaensis*.

U.S. Pat. No. 3,244,592 to T. Arai describes the culturing of *Streptomyces hygroscopicus* var. *ascomyceticus* to produce the antifungal "ascomycin", which has been shown to be the same compound as FR-900520.

There is, however, no description in the literature of the production of any FK-506 type immunosuppressive agents, which substantially lack the side effects or similar side effects to cyclosporin.

Also being searched for are drugs to prevent or counteract the inadvertent or accidental overdosage effects of FK-506 or FK-506 analogs, in a therapeutic program involving FK-506 therapy.

3. Brief Description of the Figures

FIG. 1 is an $^1H$ nuclear magnetic resonance (NMR) spectrum taken at 400 MHz of C-21 hydroxylated FR-900520 in $CDCl_3$, and also illustrates the assigned molecular structure of C-21 hydroxylated FR-900520.

SUMMARY OF THE INVENTION

It has been found that a new FK-506 antagonist, C-21 hydroxylated FR-900520, can be obtained by the fermentation of the microorganism *Streptomyces hygroscopicus* (MA 6832), ATCC No. 55166, together with the macrolide immunosuppressant FR-900520, under submerged aerobic conditions in an aqueous carbohydrate medium, containing a nitrogen nutrient, said conditions being conducted at a pH of about 7, which are sufficient to selectively hydroxylate FR-900520 at the C-21 position.

The resultant C-21 hydroxylated FR-900520 exhibits FK-506 antagonist activity, i.e. it reverses the physiological effects of FK-506 including, positive inhibition of T-cell activation, as demonstrated by the calcium ionophore (ionomycin) plus phorbol myristate acetate (PMA) induced T-cell stimulation assay, also referred to herein as the "T-cell proliferation assay".

The principle of this assay is to measure the proliferation of mouse T lymphocytes stimulated with the combination of ionomycin plus PMA. A positive sample e.g. FK-506, in this assay will inhibit T-cell proliferation, as indicated by reduced tritiated thymidine uptake. A reversal of the effects of FK-506 in this assay will indicate FK-506 antagonist activity.

In accordance with this invention, there is provided a process for producing a new FK-506 antagonist, identified as C-21 hydroxylated FR-900520, comprising the step of culturing a strain of *Streptomyces hygroscopicus*, MA 6832, ATCC No. 55166, together with FR-900520 under submerged aerobic fermentation conditions in an aqueous carbohydrate medium, containing a nitrogen nutrient, for a sufficient time to produce product C-21 hydroxylated FR-900520.

Further provided is a new FK-506 antagonist, C-21 hydroxylated FR-900520, produced by the above process which exhibits a reversal of the FK-506 positive inhibition of T-cell activation by the T-cell proliferation assay and exhibits a proton nuclear magnetic resonance spectrum illustrated in FIG. 1 and has an assigned structural formula as also identified in FIG. 1.

Also provided is a pharmaceutical composition containing a therapeutically effective amount of C-21 hydroxylated FR-900520 in combination with a pharmaceutically acceptable, substantially non-toxic carrier or excipient.

In addition, there is provided a method of use for reversing or counteracting an overdosage of FK-506 in a therapeutic program for treating human host to prevent transplantation rejection, or for treating autoimmune disease or infectious disease comprising administering to said host a therapeutically effective amount of C-21 hydroxylated FR-900520.

Furthermore there is provided a biologically pure culture of *Streptomyces hygroscopicus*, (MA 6832), ATCC No. 55166.

DETAILED DESCRIPTION OF THE INVENTION AND PREFERRED EMBODIMENTS

Figure 1:
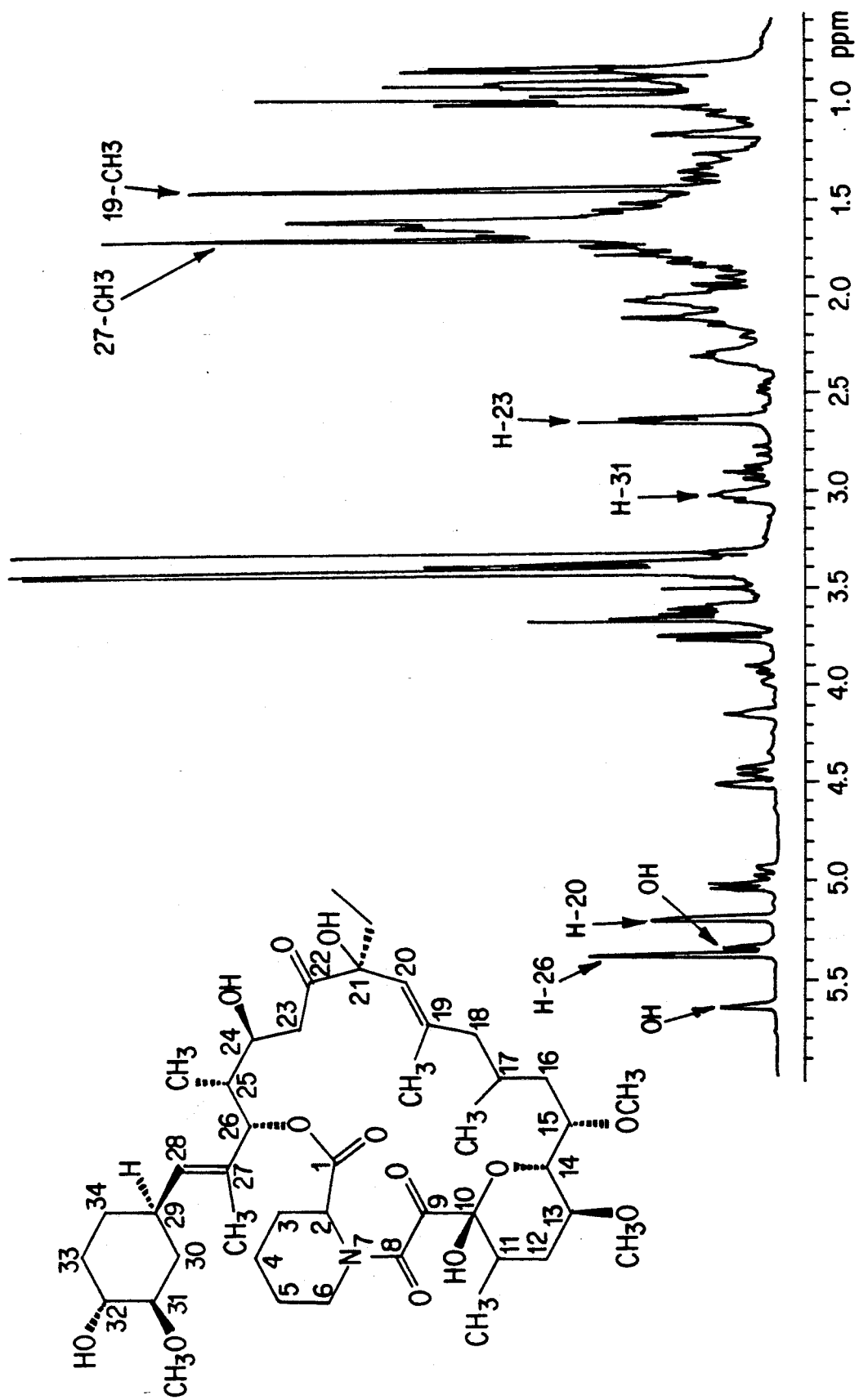

The present invention involves the fermentation of *Streptomyces hygroscopicus*, MA 6832, ATTC No. 55166, together with FR-900520 to produce C-21 hydroxylated FK-900520 (FK-520). The microorganism is currently on deposit with the American Type Culture Collection, 12301 Parklawn Drive in Rockville, Md. as ATCC No. 55166, and in the Merck Culture Collection in Rahway, N.J. as MA 6832. The physical characteristics and taxonomy, including morphological, cultural, biological and physiological characteristics are briefly described hereinbelow.

The following is a general description of strain MA6832. Observations of growth, general cultural characteristics and carbon source utilization were made in accordance with the methods of Shirling and Gottleib (Internat. J. System. Bacteriol. 16: 313–340). Chemical composition of the cells was determined using the methods of Lechevalier and Lechevalier (in Actinomycete Taxonomy, A. Dietz and D. W. Thayer, Ed. Society for Industrial Microbiology, 1980). Coloration of the culture was determined by comparison with color standards contained in the Inter-Society color council-National Bureau of Standards Centroid Color Charts (U.S. Dept. of Commerce National Bureau of Standards supplement to NBS circular 553, 1985).

Source - Garden soil, Miraflores, Madrid, Spain

Analysis of Cell Wall Composition - Peptidoglycan contains L-diaminopimelic acid, whole cell sugar analysis reveals glucose, ribose and traces of xylose.

General growth characteristics - This strain grows well on Yeast Malt Extract, Glycerol Asparagine, Inorganic Salts-Starch, Oatmeal, and Trypticase Soy agars. The strain grows at 27° and 37° C. and the strain grows well in liquid media such as Yeast Dextrose broth.

Colony morphology - (on Yeast Malt Extract Agar at 21 d) - Substrate mycelium is medium yellow (87 m. Y) and colonies are opaque, raised, erose and rubbery. The colony surface is matte to rough. Aerial mycelia appear after 5 days incubation and are white (263 White). Spore mass, when present, is dark gray to white (266 d. Gy-263 White).

Micromorphology - Aerial mycelium (0.57 $\mu$m dia.) radiates from the substrate mycelium and is straight. In mature cultures, aerial mycelia terminate in chains of spores that are borne in spirals. As the culture ages, the spore mass tends to coalesce into an amorphous mass.

Miscellaneous physiological reactions - Culture does not produce melanoid pigments. Starch is weakly hydrolyzed. Hydrogen disulfide is not produced. A diffusible yellow pigment is produced on most solid media that support vigorous growth. Carbon source utilization pattern is as follows: good utilization of cellobiose, D-fructose, inositol, $\alpha$-D-lactose, $\beta$-D-lactose, D-maltose, D-mannitol, D-mannose, d-raffinose, sucrose, D-xylose; poor utilizatin of D-arabinose, L-arabinose, L-rhamnose, L-xylose.

Diagnosis - The chemotaxonomic and morphological characteristics of this strain compares favorably with the published description of members of the genus Streptomyces. MA 6832 exhibits spore mass coloration and coalescence similar to that reported for the *Streptomyces hygroscopicus* complex. This strain is presumptively identified as a new strain of *Streptomyces hygroscopicus*.

| Carbohydrate utilization patterns of MA6832 at 21 days | |
|---|---|
| Carbon source | Utilization by MA6832 |
| D-arabinose | 1 |
| L-arabinose | 1 |
| cellobiose | 3 |
| D-fructose | 3 |
| inositol | 3 |
| $\alpha$-D-lactose | 3 |
| $\beta$-D-lactose | 3 |
| D-maltose | 3 |
| D-mannitol | 3 |
| D-mannose | 3 |
| D-raffinose | 3 |
| L-rhamnose | 1 |
| sucrose | 3 |
| D-xylose | 3 |
| L-xylose | 0 |
| a-D-glucose (control) | 3 |

3 = good utilization, 2 = moderate utilization,
1 = poor utilization, 0 = no utilization

| Cultural characteristics of MA6832 at 21 days | | |
|---|---|---|
| Medium | Amount of Growth MA6832 | Aerial Mycelium MA6832 |
| Yeast Extract Malt Extract | good | Dark gray (266 d.Gy) Spiral sporophores, coalesce into amorphous masses. |
| Gluocose Asparagine | good | Brownish gray (64 brGy) Spiral sporophores, coalesce into amorphous masses. |
| Inorganic Salts Starch | good | Black (267 Black) Spiral sporophores, coalesce into amorphous masses. Starch hydrolyzed. |
| Oatmeal | good | Black (267 Black) Spiral sporophores, coalesce into amorphous masses. |
| Sigma Water | sparse | Dark gray (266 dGy) Spiral sporophores, coalesce into amorphous masses. |
| Czpak | good | Light gray (264 lGy) Spiral sporophores, coalesce into amorphous masses. |
| Peptone Iron | good | |
| Medium | Soluble Pigments MA6832 | Substrate Mycelium MA6832 |
| Yeast Extract Malt Extract | Yellow | Medium yellow (87 m.Y) |
| Glucose Asparagine | Yellow | Pale yellow (89 p.Y) |
| Inorganic Salts Starch | Yellow | Light gray olive (109 l.gy.Ol) |
| Oatmeal | Yellow | Olive gray (113 01Gy) |
| Sigma Water | none noted | Black (267 Black) |
| Czpak | none noted | Light yellow (86 l.Y) |
| Peptone Iron | melanin negative, $H_2S$ negative | |

The present invention process can be practiced with any C-21 hydroxylating FR-900520 producing strain of *Streptomyces hygroscopicus*, and particularly preferred is the ATCC No. 55166 strain (MA6832).

In general, C-21 hydroxylated FR-900520 can be produced by culturing (fermentation) the *Streptomyces hygroscopicus* strain capable of hydroxylating FR-900520 in the C-21 position, in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, raffinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, and also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, polypropylene glycol, mineral oil or silicone may be added.

The FR-900520 starting material can be obtained by the fermentation of *S. hygroscopicus* var. *ascomyceticus*, ATCC No. 14891, as described in U.S. Pat. No. 3,244,592, and the fermentation of *S. hygroscopicus* subsp. *yakushimaensis* No. 7278, to produce FR-900520, as described in EPO Publication No. 0184162 to Fujisawa, and U.S. Pat. No. 4,894,366.

As to the conditions for the production of C-21 hydroxylated FR-900520 in massive amounts, submerged aerobic cultural conditions are preferred therefor. For the production in small amounts, a shaking of surface culture in a flask or bottle is employed. Furthermore, when the growth is carried out in large tanks, it is preferable to use the vegetative form of the organism for inoculation in the production tanks in order to avoid growth lag in the process of production of C-21 hydroxylated FR-900520. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of C-21 hydroxylated FR-900520 and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 10 hours to 20 hours, which may be varied according to fermentation conditions and scales. Preferably, the production cultures are incubated for about 17 hours at 27° C. on a rotary shaker operating at 220 rpm, wherein the pH of the fermentation medium is maintained at 7.0 to harvest.

Preferred culturing/production media for carrying out the fermentation include the following media:

|  | g/liter |
|---|---|
| Seed Medium | |
| Dextrose | 1.0 |
| Dextrin | 10.0 |
| Beef Extract | 3.0 |
| Ardamine pH | 5.0 |
| NZ Amine Type E | 5.0 |
| MgSO$_4$.7H$_2$O | 0.05 |
| K$_2$HPO$_4$ | 0.37 |
| Adjust pH to 7.1 | |
| Add CaCO$_3$ 0.5 g/l | |
| Transformation Medium B | |
| Glucose | 4 |
| Malt Extract | 10 |
| Yeast Extract | 4 |
| Nutrient Broth | 4 |
| Adjust pH to 7.0 | |

The produced C-21 hydroxylated FK-900520 can be recovered from the culture medium by conventional means which are commonly used for the recovery of other known biologically active substances. The C-21 hydroxylated FR-900520 substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

The product C-21 hydroxylated FR-900520 from the fermentation exhibits antagonist activity versus the FK-506 immunosuppressive activity by the "T-cell proliferation assay" and possesses utility on this basis and exhibits the following physical characteristics:
1. White amorphous powder
2. Solubility in methanol
3. Molecular weight of 807, as determined by FAB mass spectroscopy (observed M+Li=814), is consistent with the assigned structure in FIG. 1.

The C-21 hydroxylated FR-900520 obtained according to the fermentation processes as explained above can be isolated and purified in a conventional manner, for example, extraction, precipitation, fractional crystallization, recrystallization, chromatography, and the like.

It is to be noted that in the aforementioned fermentation reactions and the post-treatment of the fermentation mixture therein, the conformer and/or stereo isomer(s) of C-21 hydroxylated FR-900520 due to asymmetric carbon atom(s) or double bond(s) of the C-21 hydroxylated FR-900520 may occasionally be transformed into the other conformer and/or stereoisomer(s), and such cases are also included within the scope of the present invention.

The C-21 hydroxylated FR-900520 of the present invention possesses antagonist pharmacological activity therefore is useful or an antidote versus FK-506 for inadvertent or accidental overdosage of FK-506 in a Therapeutic program involving FK-506 designed for the treatment and prevention of the transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosus, Hashimoto's thyroiditis, multiple sclerosis, myasthenia gravis, type I diabetes, uveitis, and the like.

The pharmaceutical composition of this invention can be used in the form of a pharmaceutical preparation, for example, in solid, semisolid or liquid form, which contains the C-21 hydroxylated FR-900520, of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to a human, it is preferable to apply it by parenteral or enteral administration. While the dosage of therapeutically effective amount of the C-21 hydroxylated FR-900520, varies from, and also depends upon the age and condition of each individual patient to be treated, and the amount of FK-506 administered, which should be equal to the amount of FK-506 overdosage and greater, a daily dose (calculated on the basis of a 70 kg man) of about 0.01–1000 mg, preferably 0.1–500 mg and more preferably 0.5–100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples are given for the purpose of illustrating the present invention and should not be construed as being limitations on the scope or spirit of the instant invention.

EXAMPLE 1

Microorganism and Culture Conditions

The lyophilized culture (MA 6832) ATCC No. 55166 was used to inoculate a 250 ml baffled shake flask containing 50 ml of an autoclaved (sterilized) seed medium consisting of (in units of grams/liter) dextrin 10.0, dextrose 1.0, beef extract 3.0, ardamine PH (Yeast Products, Inc.) 5.0, N-Z Amine type E 5.0, $MgSO_4.7H_2O$ 0.05, $KH_2PO_4$ 0.37, and $CaCO_3$ 0.5. The pH of the seed medium was adjusted to 7.1 before autoclaving. The seed was incubated in the seed medium at 27° C. for 48 hours on a rotary shaker operating at 220 rpm. Alternatively, when frozen vegetative mycelia or a slant source is used, the culture is incubated in the seed medium at 27° C. for 48 hours at 220 rpm. A 2.5 ml aliquot of the resulting seed medium was used to inoculate a 250 ml non-baffled shake flask containing 50 ml of the following previously autoclaved (sterilized) fermentation medium. FR-900520 was added as a solution in dimethylsulfoxide to achieve a final concentration of 0.1 mg/ml concentration. The shake flask contents were subsequently incubated for 18 hrs. at 27° C. on a rotary shaker operating at 220 rpm:

1. Fermentation medium consisted of (in grams/liter) dextrose 4.0; malt extract 10.0; yeast extract 4.0; nutrient broth 4.0; where the pH was adjusted to 7.0 before autoclaving.

Assay Procedure

The reaction was monitored by means of HPLC of the time samples. The whole broth was mixed with equal volume of MeOH. The mixture was shaken for ten minutes. The filtered supernatant was used for the HPLC assay. In addition to the biotransformation samples, a culture blank was worked up according to the same procedure. The comparison between the HPLC charts of the biotransformation sample and the culture blank allowed the identification of the metabolite peaks.

The chromatographic resolution was tested on RAININ MICROSORB $C_8$ and $C_{18}$, and DuPONT ZORBAX CN columns. The separation on the ZORBAX CN column (4.6 mm × 25 cm). was superior. The elution was performed at a flow rate of 0.9 ml/min in the gradient mode with the solvents being A: 10 mM $H_3PO_4$ and B: $CH_3CN$-water (17:3 v/v). The gradient profile was as follows:

| Time (min.) | B % |
| --- | --- |
| 0 | 30 |
| 2 | 30 |
| 18 | 80 |
| 20 | 100 |
| 24 | 100 |
| 25 | 30 |

The pilot wavelength of the diode array detector was 205 nm.

Isolation

The harvested whole broth sample was mixed with one volume of MeOH. The supernatant was separated. MeOH was stripped from the mixture by distillation in vacuo. The aqueous residue was extracted with two volumes of $CH_2Cl_2$. The organic phase was separated and evaporated to dryness. The dry residue was redissolved in a small volume of MeOH (1/100 of the volume of the whole broth) for assay and subsequent prep. HPLC separation. The initial prep. HPLC separation was carried out on a Beckman Ultrasphare $C_{18}$ column (10 mm × 25 cm). The gradient profile was the same as that described under the ASSAY PROCEDURES scaled to 45 minutes and at a flow rate of 3.0 ml/min. Fractions were collected in every two minutes. Phosphoric acid was neutralized with a few drops of $NH_4OH$ before evaporation to dryness. The dry residues were redissolved in MeOH (1.00 ml) and evaluated in analytical HPLC. The fractions containing suspected metabolites were submitted to the IL-2 assay. The samples testing positive in the IL-2 assay were further purified in a second prep. HPLC on a Beckman Cyano column (10 mm × 25 cm) and using the same elution procedure as in the first prep. HPLC.

C-21 hydroxylated FR-900520 had a retention time of 16.27 min.

MASS SPECTRAL DATA

Mass spectral examination of the above biotransformation product obtained by the incubation of FR-900520 with culture MA6832 indicates that hydroxylation has occurred. NMR data, as shown in the spectrum of FIG. 1, is consistent with hydroxylation occurring at C-21. Key features are the upfield displacement of the 19-methylpeak, now at 1.43 ppm, the absence of a typical H-20 doublet and the presence of a slightly broadened singlet at 5.20 ppm identified as H-20 in a modified enviroment. The singlet character implied that H-21 was absent. The chemical shift of 5.20 ppm is 0.2 ppm downfield from the position of H-20 in FR-900520. This inference was reinforced by the results of double irradiation experiment in which irradiating the 36-methyl collapsed the 35-methylene to a singlet.

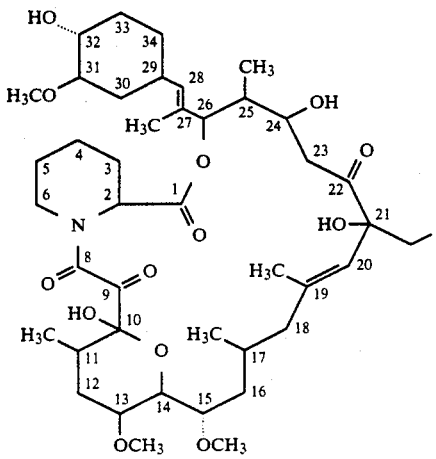

C-21 Hydroxylated FR-900520 The assigned molecular structure is shown above and in FIG. 1.

EXAMPLE 2

T-Cell Proliferation Assay

1. Sample Preparation

Purified C-21 hydroxylated FR-900520, as prepared by HPLC above, was dissolved in absolute ethanol at 1 mg/ml.

2. Assay

Spleens from C57B1/6 mice were taken under sterile conditions and gently dissociated in ice-cold RPMI 1640 culture medium (GIBCO, Grand Island, N.Y.) supplemented with 10% heat-inactivated fetal calf serum (GICO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lymphocytes were then isolated by separation of the cell suspension on nylon wool columns as follows: nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$ M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The control, being the medium without test drug, and various below-indicated dilutions of the sample (above-described purified C-21 hydroxylated FR-900520) to be tested were then added in triplicate wells at 20 µl/well. FR-900506 was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as percent inhibition of tritiated thymidine uptake (proliferation) as follows:

$$\% \text{ Inhibition} = 100 - \frac{\text{Mean cpm sample tested}}{\text{Mean cpm control medium}} \times 100.$$

The results of % inhibition at various concentrations of C-21 hydroxylated FR-900520 ("21-OH590") are presented in the following Table:

TABLE

Effects of 21-OH-590 on the proliferative response of mouse T-cells activated with ionomycin + PMA

| Sample | Concentration (ng/ml) | % Inhibition No FK-506 | % Inhibition + FK-506 (1.2 nM) |
|---|---|---|---|
| Medium (control) | | 0 | 97 |
| 21-OH-590 | 1000 | 0 | 0 |
| | 500 | 0 | 0 |
| | 250 | 0 | 63 |
| | 125 | 0 | 94 |

The proliferative response of ionomycin + PMA activated T cells was measured by incorporation of tritiated thymidine As seen by the data 21-OH-590 is a pure antagonist of FK-506 immunosuppression.

Notes:
1. Mouse T cell cultures were pulsed with $^3$H-thymidine for 4 hours prior to harvesting at 48 hours.
2. Standard FR-900506 (10 ng/ml) gave 99% inhibition.

What is claimed is:

1. A process for producing an FK-506 antagonist, identified as C-21 hydroxylated FK-900520, comprising the step of culturing a strain of *Streptomyces hygroscopicus*, ATCC No.. 55166, together with FR-900520 under submerged aerobic fermentation conditions in an aqueous carbohydrate medium containing a nitrogen nutrient for a sufficient time to produce C-21 hydroxylated FR-900520.

2. The unfiltered broth produced by the process of claim 1, containing C-21 hydroxylated FK-900520 and the microorganism.

3. The FK-506 antagonist product produced by the above-described process of claim 1.

4. A pharmaceutical composition containing a therapeutically effective amount of C-21 hydroxylated FK-900520 in combination with a pharmaceutically acceptable, substantially non-toxic carrier or excipient.

5. A method of use for treating a human host to prevent overdosage of FK-506 during therapy to prevent transplantation rejection, or for treating autoimmune disease or infectious disease comprising administering to said host a therapeutically effective amount of C-21 hydroxylated FK-900520.

6. An FK-506 antagonist, C-21 hydroxylated FK-900520, which exhibits a proton nuclear magnetic spectrogram as depicted in FIG. 1.

* * * * *